(12) United States Patent
Shimokawatoko et al.

(10) Patent No.: US 8,796,231 B2
(45) Date of Patent: Aug. 5, 2014

(54) PEST CONTROL COMPOSITION

(75) Inventors: Yasutaka Shimokawatoko, Kobe (JP);
Katsuya Natsuhara, Toyonaka (JP);
Tetsuo Tanikawa, Kawasaki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/579,681

(22) PCT Filed: Feb. 18, 2011

(86) PCT No.: PCT/JP2011/054222
§ 371 (c)(1),
(2), (4) Date: Sep. 6, 2012

(87) PCT Pub. No.: WO2011/102550
PCT Pub. Date: Aug. 25, 2011

(65) Prior Publication Data
US 2013/0005671 A1 Jan. 3, 2013

(30) Foreign Application Priority Data
Feb. 19, 2010 (JP) ................................. 2010-034887

(51) Int. Cl.
*A61K 31/70* (2006.01)
*A01N 43/22* (2006.01)

(52) U.S. Cl.
CPC ...................................... *A01N 43/22* (2013.01)
USPC ......................................................... 514/28

(58) Field of Classification Search
None
See application file for complete search history.

(56) References Cited

U.S. PATENT DOCUMENTS

| 5,362,634 | A | * | 11/1994 | Boeck et al. ..................... 435/76 |
| 5,478,855 | A | * | 12/1995 | Suzuki et al. .................. 514/374 |
| 6,919,464 | B1 | | 7/2005 | Crouse et al. |
| 2010/0055084 | A1 | | 3/2010 | Gutsche et al. |
| 2010/0204167 | A1 | | 8/2010 | Fischer et al. |

FOREIGN PATENT DOCUMENTS

| CN | 101489388 A | 7/2009 |
| CN | 101646349 A | 2/2010 |
| EP | 0 375 316 B1 | 12/1994 |
| JP | 11-506117 A | 6/1999 |
| JP | 2006-131516 A | 5/2006 |
| JP | 2009-132670 A | 6/2009 |
| JP | 2009-542744 A | 12/2009 |
| WO | WO 93/22297 A1 | 11/1993 |
| WO | WO 97/00265 A1 | 1/1997 |
| WO | WO 2009/103650 A1 | 8/2009 |

OTHER PUBLICATIONS

International Searchi Report for PCT/JP2011/054222 dated Mar. 29, 2011.
Written Opinion of the International Searching Authority for PCT/JP2011/054222 dated Mar. 29, 2011.
International Preliminary Report on Patentability for International Patent Application No. PCT/JP2011/054222, dated Aug. 21, 2012.
The Office Action (including English translation), dated Aug. 29, 2013, issued in corresponding Chinese Patent Application No. 201180010083.7.
The Search Report, dated Jul. 16, 2013, issued in corresponding European Patent Application No. 11744832.4.
The Second Office Action (including English translation), dated Feb. 24, 2014, issued in the corresponding Chinese Patent Application No. 201180010083.7.
The Third Office Action (including an English translation), dated May 20, 2014, issued in the corresponding Chinese Patent Application No. 201180010083.7.

* cited by examiner

*Primary Examiner* — Traviss C McIntosh, III
(74) *Attorney, Agent, or Firm* — Birch, Stewart, Kolasch & Birch, LLP

(57) ABSTRACT

Disclosed is a pest control composition having an excellent controlling effect on pests, which comprises etoxazole and a compound represented by the formula (I): wherein, $R^1$ is a hydrogen atom or a methyl group, $R^2$ is a hydrogen atom, a C1-C4 alkyl group, a C1-C4 haloalkyl group, or a (C1-C4 alkyl)carbonyl group, $R^3$ is a hydrogen atom, a C1-C4 alkyl group, a C1-C4 haloalkyl group, or a (C1-C4 alkyl)carbonyl group, $R^4$ is a hydrogen atom, a C1-C4 alkyl group, a C1-C4 haloalkyl group, or a (C1-C4 alkyl)carbonyl group, $R^5$ is a hydrogen atom, a C1-C4 alkyl group, or a C1-C4 alkylamino group, $R^6$ is a hydrogen atom or a methyl group, $R^7$ is a methyl group or an ethyl group, $R^8$ is an amino group, a C1-C4 alkylamino group, or a di(C1-C4 alkyl)amino group, and $X^1$ and $X^2$ are hydrogen atoms or $X^1$ and $X^2$ together form a single bond.

(I)

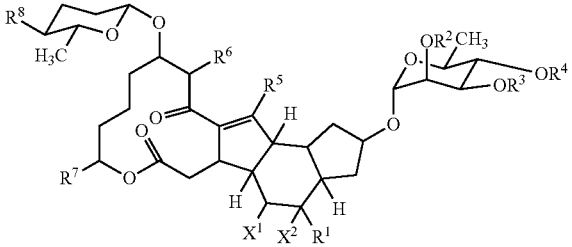

6 Claims, No Drawings

PEST CONTROL COMPOSITION

TECHNICAL FIELD

The present invention relates to a pest control composition and a pest control method.

BACKGROUND ART

Heretofore, various compounds for controlling pests have been found or developed, and pest control agents comprising the compounds as the active ingredients have been used in practice.

Etoxazole, 2-(2,6-difluorophenyl)-4-[4-(1,1-dimethylethyl)-2-ethoxyphenyl]-4,5-dihydrooxazole) is known as the active ingredient of a pest control agent (see, e.g., Patent Literature 1).

Also, a compound represented by the formula (I):

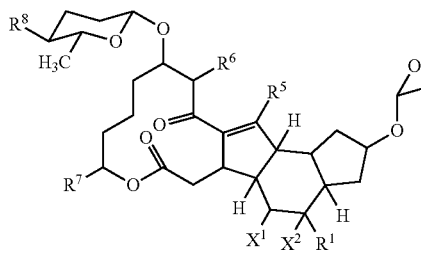

(I)

wherein,
R$^1$ is a hydrogen atom or a methyl group,
R$^2$ is a hydrogen atom, a C1-C4 alkyl group, a C1-C4 haloalkyl group, or a (C1-C4 alkyl)carbonyl group,
R$^3$ is a hydrogen atom, a C1-C4 alkyl group, a C1-C4 haloalkyl group, or a (C1-C4 alkyl)carbonyl group,
R$^4$ is a hydrogen atom, a C1-C4 alkyl group, a C1-C4 haloalkyl group, or a (C1-C4 alkyl)carbonyl group,
R$^5$ is a hydrogen atom, a C1-C4 alkyl group, or a C1-C4 alkylamino group,
R$^6$ is a hydrogen atom or a methyl group,
R$^7$ is a methyl group or an ethyl group,
R$^8$ is an amino group, a C1-C4 alkylamino group, or a di(C1-C4 alkyl)amino group, and
X$^1$ and X$^2$ are hydrogen atoms or X$^1$ and X$^2$ together form a single bond, is known as the active ingredient of a pest control agent (see, e.g., Patent Literatures 2 and 3).

CITATION LIST

Patent Literature

Patent Literature 1: WO93/22297
Patent Literature 2: EP375316A
Patent Literature 3: WO97/00265

SUMMARY OF INVENTION

Technical Problem

An object of the present invention is to provide a pest control composition having an excellent control effect on pests and a pest control method.

Solution to Problem

The present inventors studied intensively and as a result, found that a combination of etoxazole and a compound represented by the following formula (I) has an excellent control effect on pests. Thus, the present invention was completed.

The present invention provides:
(1) A pest control composition comprising etoxazole and a compound represented by the formula (I):

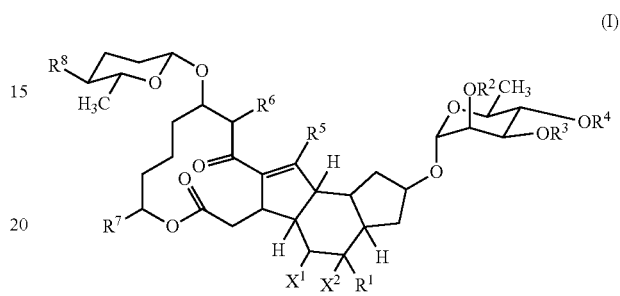

(I)

wherein,
R$^1$ is a hydrogen atom or a methyl group,
R$^2$ is a hydrogen atom, a C1-C4 alkyl group, a C1-C4 haloalkyl group, or a (C1-C4 alkyl)carbonyl group,
R$^3$ is a hydrogen atom, a C1-C4 alkyl group, a C1-C4 haloalkyl group, or a (C1-C4 alkyl)carbonyl group,
R$^4$ is a hydrogen atom, a C1-C4 alkyl group, a C1-C4 haloalkyl group, or a (C1-C4 alkyl)carbonyl group,
R$^5$ is a hydrogen atom, a C1-C4 alkyl group, or a C1-C4 alkylamino group,
R$^6$ is a hydrogen atom or a methyl group,
R$^7$ is a methyl group or an ethyl group,
R$^8$ is an amino group, a C1-C4 alkylamino group, or a di(C1-C4 alkyl)amino group, and
X$^1$ and X$^2$ are hydrogen atoms or X$^1$ and X$^2$ together form a single bond;
(2) The pest control composition according to the above (1), wherein the weight ratio of etoxazole to the compound represented by the formula (I) is 100:1 to 1:100;
(3) The pest control composition according to the above (1) or (2), wherein the compound represented by the formula (I) is spinosad or spinetoram;
(4) A pest control method which comprises applying effective amounts of etoxazole and a compound represented by the formula (I) to a pest or an area where a pest lives:

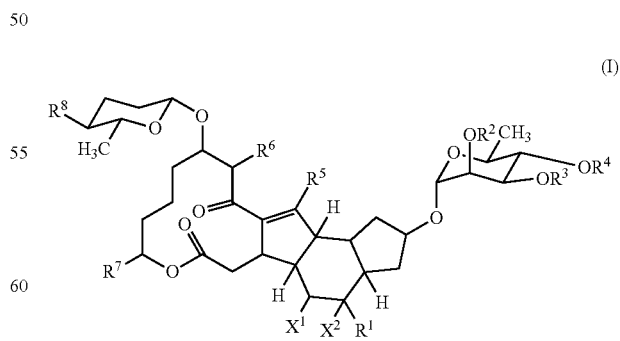

(I)

wherein,
R$^1$ is a hydrogen atom or a methyl group,
R$^2$ is a hydrogen atom, a C1-C4 alkyl group, a C1-C4 haloalkyl group, or a (C1-C4 alkyl)carbonyl group, R³ is a hydrogen atom, a C1-C4 alkyl group, a C1-C4 haloalkyl group, or a (C1-C4 alkyl)carbonyl group,
R⁴ is a hydrogen atom, a C1-C4 alkyl group, a C1-C4 haloalkyl group, or a (C1-C4 alkyl)carbonyl group,
R⁵ is a hydrogen atom, a C1-C4 alkyl group, or a C1-C4 alkylamino group,
R⁶ is a hydrogen atom or a methyl group,
R⁷ is a methyl group or an ethyl group,
R⁸ is an amino group, a C1-C4 alkylamino group, or a di(C1-C4 alkyl)amino group, and
X¹ and X² are hydrogen atoms or X¹ and X² together form a single bond;
(5) The pest control method according to the above (4), wherein the weight ratio of etoxazole to the compound represented by the formula (I) is 100:1 to 1:100; and
(6) The pest control method according to the above (4) or (5), wherein the compound represented by the formula (I) is spinosad or spinetoram.

Effects of Invention

According to the present invention, a pest control composition having an excellent control effect on pests and a pest control method can be provided.

DESCRIPTION OF EMBODIMENTS

The pest control composition of the present invention contains etoxazole and a compound represented by the above formula (I).
Etoxazole can be produced by a process described in WO93/22297.
The compound represented by the formula (I) is, for example, described in EP375316A or WO97/00265 and can be produced by a process described therein.
In the formula (I), examples of R², R³, R⁴, R⁵ and R⁸ are as follows.
Examples of the "C1-C4 alkyl group" represented by R², R³, R⁴ or R⁵ include a methyl group, an ethyl group, propyl group, a butyl group, a 1-methylethyl group and a 1,1-dimethylethyl group.
Examples of the "C1-C4 haloalkyl group" represented by R², R³ or R⁴ include a 2,2,2-trifluoroethyl group. As used herein, the term "halo" means fluoro, chloro, bromo or iodo.
Examples of the "(C1-C4 alkyl)carbonyl group" represented by R², R³ or R⁴ include a methylcarbonyl group, an ethylcarbonyl group, a propylcarbonyl group, and a butylcarbonyl group.

Examples of the "C1-C4 alkylamino group" represented by R⁵ or R⁸ include a methylamino group, an ethylamino group, a propylamino group, and a butylamino group.
Examples of the "di(C1-C4 alkyl)amino group" represented by R⁸ include a dimethylamino group, a diethylamino group, a methylethylamino group, and a dipropylamino group.
The compound represented by the formula (I) wherein X¹ and X² together form a single bond is particularly a compound represented by the formula (I-a):

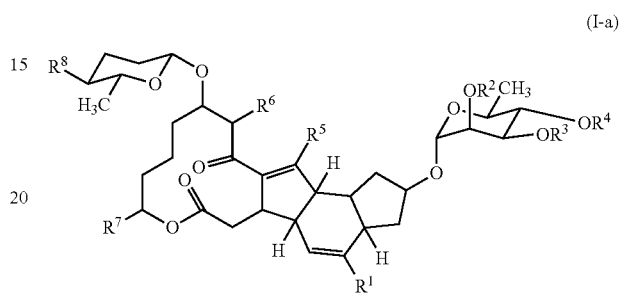

(I-a)

wherein R¹, R², R³, R⁴, R⁵, R⁶, R⁷ and R⁸ are as defined above.
Examples of a compound represented by the formula (I) include the following compounds.
Compounds represented by the formula (I):

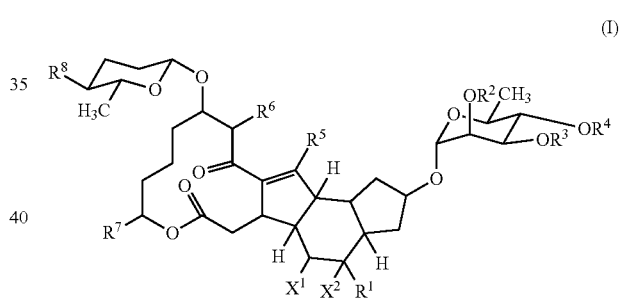

(I)

wherein, R¹, R³, R⁴, R⁵, R⁶, R⁷, R⁸, X¹ and X² represent any combination shown in Table 1.

TABLE 1

| No. | R¹ | R² | R³ | R⁴ | R⁵ | R⁶ | R⁷ | R⁸ | X¹ X² |
|---|---|---|---|---|---|---|---|---|---|
| 1 | H | CH₃ | CH₃ | CH₃ | H | CH₃ | CH₂CH₃ | N(CH₃)₂ | single bond |
| 2 | H | CH₃ | CH₃ | CH₃ | H | CH₃ | CH₂CH₃ | NH(CH₃) | single bond |
| 3 | H | CH₃ | CH₃ | CH₃ | H | CH₃ | CH₂CH₃ | NH₂ | single bond |
| 4 | CH₃ | CH₃ | CH₃ | CH₃ | H | CH₃ | CH₂CH₃ | N(CH₃)₂ | single bond |
| 5 | H | CH₃ | CH₃ | CH₃ | H | CH₃ | CH₃ | N(CH₃)₂ | single bond |
| 6 | H | CH₃ | CH₃ | CH₃ | H | H | CH₂CH₃ | N(CH₃)₂ | single bond |
| 7 | H | H | CH₃ | CH₃ | H | CH₃ | CH₂CH₃ | N(CH₃)₂ | single bond |
| 8 | H | CH₃ | H | CH₃ | H | CH₃ | CH₂CH₃ | N(CH₃)₂ | single bond |
| 9 | H | CH₃ | CH₃ | H | H | CH₃ | CH₂CH₃ | N(CH₃)₂ | single bond |
| 10 | CH₃ | CH₃ | H | CH₃ | H | CH₃ | CH₂CH₃ | N(CH₃)₂ | single bond |
| 11 | H | CH₃ | H | CH₃ | H | CH₃ | CH₂CH₃ | NH(CH₃) | single bond |
| 12 | CH₃ | CH₃ | H | CH₃ | H | CH₃ | CH₂CH₃ | NH(CH₃) | single bond |
| 13 | CH₃ | CH₃ | CH₃ | H | H | CH₃ | CH₂CH₃ | N(CH₃)₂ | single bond |
| 14 | H | CH₃ | H | H | H | CH₃ | CH₂CH₃ | N(CH₃)₂ | single bond |
| 15 | CH₃ | H | CH₃ | CH₃ | H | CH₃ | CH₂CH₃ | N(CH₃)₂ | single bond |
| 16 | H | H | CH₃ | CH₃ | H | CH₃ | CH₂CH₃ | NH(CH₃) | single bond |
| 17 | H | H | CH₃ | CH₃ | H | CH₃ | CH₂CH₃ | N(CH₃)₂ | single bond |
| 18 | H | H | H | CH₃ | H | CH₃ | CH₂CH₃ | N(CH₃)₂ | single bond |
| 19 | H | H | CH₃ | H | H | CH₃ | CH₂CH₃ | N(CH₃)₂ | single bond |

TABLE 1-continued

| No. | $R^1$ | $R^2$ | $R^3$ | $R^4$ | $R^5$ | $R^6$ | $R^7$ | $R^8$ | $X^1$ | $X^2$ |
|---|---|---|---|---|---|---|---|---|---|---|
| 20 | $CH_3$ | H | $CH_3$ | H | H | $CH_3$ | $CH_2CH_3$ | $N(CH_3)_2$ | single bond | |
| 21 | $CH_3$ | $CH_3$ | H | H | H | $CH_3$ | $CH_2CH_3$ | $N(CH_3)_2$ | single bond | |
| 22 | H | $CH_3$ | $CH_3$ | H | H | $CH_3$ | $CH_3$ | $N(CH_3)_2$ | single bond | |
| 23 | H | $CH_3$ | $CH_2CH_3$ | $CH_3$ | H | $CH_3$ | $CH_2CH_3$ | $N(CH_3)_2$ | H | H |
| 24 | $CH_3$ | $CH_3$ | $CH_2CH_3$ | $CH_3$ | H | $CH_3$ | $CH_2CH_3$ | $N(CH_3)_2$ | single bond | |

In Table 1, Compound No. 1 is also known as spinosyn A, Compound No. 4 is also known as spinosyn D, Compound No. 23 is also known as spinetoram J, and Compound No. 24 is also known as spinetoram L.

A mixture of Compound No. 1 (spinosyn A) and Compound No. 4 (spinosyn D) is known by the general name spinosad, and known as an active ingredient of a pesticide. A mixture of Compound No. 23 (spinetoram J) and Compound No. 24 (spinetoram L) is known by the general name spinetoram, and known as an active ingredient of a pesticide. Spinosad or spinetoram can be also used in the present invention.

In spinosad, the mixing weight ratio of spinosyn A to spinosyn D is usually 50:50 to 95:5, preferably 70:20 to 95:5. Spinosad can be produced, for example, by process described in EP375316A.

In spinetoram, the mixing weight ratio of spinetoram J to spinetoram L is usually 50:50 to 90:10, preferably 70:30 to 90:10. Spinetoram can be produced, for example, by a process described in WO97/00265.

In the pest control composition of the present invention, the weight ratio of etoxazole to the compound represented by the formula (I) is usually 100:1 to 1:100, preferably 10:1 to 1:10, more preferably 5:1 to 1:5.

The pest control composition of the present invention may be a simple mixture of etoxazole and the compound represented by the formula (I). However, the pest control composition of the present invention is usually prepared by mixing etoxazole and the compound represented by the formula (I) and an inert carrier, and if necessary a surfactant and other formulation additives, and then formulating the mixture into a dosage form such as an oil solution, an emulsifiable concentrate, a suspension concentrate, a wettable powder, a water dispersible granule, a dust, or a granule.

The pest control composition of the present invention contains etoxazole and the compound represented by the formula (I) in a total amount of usually 0.01 to 90% by weight, preferably 0.1 to 80% by weight.

Examples of the inert carrier include a solid carrier, a liquid carrier and a gaseous carrier.

Examples of the solid carrier include fine powders and granules of minerals (e.g. kaolin clay, attapulgite clay, bentonite, montmorillonite, acidic white clay, pyrophyllite, talc, diatomaceous earth, and calicite), natural organic substances (e.g. corncob flour, and walnut shell flour), synthetic organic substances (e.g. urea, and urea formaldehyde resin), salts (e.g. calcium carbonate, and ammonium sulfate), and synthetic inorganic substances (e.g. synthetic hydrated silicon oxide).

Examples of the liquid carrier include aromatic hydrocarbons (e.g. xylene, alkylbenzene, and methyl naphthalene), alcohols (e.g. 2-propanol, ethylene glycol, propylene glycol, and ethylene glycol monoethyl ether), ketones (e.g. acetone, cyclohexanone, and isophorone), vegetable oils (e.g. soybean oil, and cotton oil), petroleum-based aliphatic hydrocarbons, esters, dimethylsulfoxide, acetonitrile, and water.

Examples of the gaseous carrier include fluorocarbon, butane gas, liquefied petroleum gas (LPG), dimethyl ether, and carbon dioxide.

Examples of the surfactant include anionic surfactants (e.g. alkyl sulfate ester salts, alkylaryl sulfonates, dialkyl sulfosuccinates, polyoxyethyle alkylaryl ether phosphate ester salts, ligninsulfonates, naphthalene sulfonate formaldehyde polycondensates, styrene-acrylate copolymers, and methyl oleyl taurate sodium salts), nonionic surfactants (e.g. polyoxyethylene alkylaryl ethers, polyoxyethylene alkylpolyoxypropylene block copolymers, and sorbitan fatty acid esters), and cationic surfactants (e.g. alkyl trimethyl ammonium salts).

Examples of the formulation additives include water-soluble polymers (e.g., polyvinyl alcohol, and polyvinyl pyrrolidone), polysaccharides [e.g., gum arabic, alginic acid and a salt thereof, CMC (carboxymethyl cellulose), and xanthane gum], inorganic substances (e.g. aluminum magnesium silicate, smectite, and alumina-sol), preservatives (e.g. 5-chloro-2-methyl-4-isothiazolin-3-one, 1,2-benzothiazolin-3-one, and 2-bromo-2-nitropropane-1,3-diol), colorants, and stabilizers [e.g. PAP (isopropyl acid phosphate), and BHT (2,6-di-tert-butyl-4-methylphenol)].

Examples of pests against which the pest control composition of the present invention exhibits a controlling effect include arthropods such as insects and mites, and nemathelminthes such as nematodes, as listed below.

Hemiptera:

Delphacidae such as *Laodelphax striatellus*, *Nilaparvata lugens*, and *Sogatella furcifera*; Deltocephalidae such as *Nephotettix cincticeps*, and *Nephotettix virescens*; Aphididae such as *Aphis gossypii*, *Myzus persicae*, *Brevicoryne brassicae*, *Macrosiphum euphorbiae*, *Aulacorthum solani*, *Rhopalosiphum padi*, and *Toxoptera citricidus*; Pentatomidae such as *Nezara antennata*, *Riptortus clavetus*, *Leptocorisa chinensis*, *Eysarcoris parvus*, *Halyomorpha mista*, and *Lygus lineolaris*; Aleyrodidae such as *Trialeurodes vaporariorum*, *Bemisia tabaci*, *Bemisia argentifolii*, and *Aleurocanthus spiniferus*; Coccidae such as *Aonidiella aurantii*, *Comstockaspis perniciosa*, *Unaspis citri*, *Ceroplastes rubens*, *Icerya purchasi*, and *Pseudaulacaspis pentagona*; Tingidae; Psyllidae; etc.

Lepidoptera:

Pyralidae such as *Chilo suppressalis*, *Tryporyza incertulas*, *Cnaphalocrocis medinalis*, *Notarcha derogata*, *Plodia interpunctella*, *Ostrinia furnacalis*, *Ostrinia nubilalis*, *Hellula undalis*, and *Pediasia teterrellus*; Noctuidae such as *Spodoptera litura*, *Spodoptera exigua*, *Pseudaletia separata*, *Mamestra brassicae*, *Agrotis ipsilon*, *Plusia nigrisigna*, *Thoricoplusia* spp., *Heliothis* spp., and *Helicoverpa* spp.; Pieridae such as *Pieris rapae*; Tortricidae such as *Adoxophyes* spp., *Grapholita molesta*, *Leguminivora glycinivorella*, *Matsumuraeses azukivora*, *Adoxophyes orana fasciata*, *Adoxophyes* sp., *Homona magnanima*, *Archips fuscocupreanus*, and *Cydia pomonella*; Gracillariidae such as *Caloptilia theivora*, and *Phyllonorycter ringoneella*; Carposimidae such as *Carposina niponensis*; Lyonetiidae such as *Lyonetia* spp.;

Lymantriidae such as *Lymantria* spp., and *Euproctis* spp.; Yponomeutidae such as *Plutella xylostella*; Gelechiidae such as *Pectinophora gossypiella*, and *Phthorimaea operculella*; Arctiidae such as *Hyphantria cunea*; Tineidae such as *Tinea translucens*, and *Tineola bisselliella*; etc.

Thysanoptera:

Thripidae such as *Frankliniella occidentalis, Thrips palmi, Scirtothrips dorsalis, Thrips tabaci, Frankliniella intonsa*, and *Frankliniella fusca*; etc.

Diptera:

*Musca domestica, Culex pipiens pallens, Tabanus trigones, Hylemya antiqua, Hylemya platura, Anopheles sinensis, Agromyza oryzae, Hydrellia griseola, Chlorops oryzae*; Agromyzidae such as *Liriomyza trifolii; Dacus cucurbitae, Ceratitis capitata*; etc.

Coleoptera:

*Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Lasioderma serricorne, Anthrenus verbasci, Tribolium castaneum, Lyctus brunneus, Anoplophora malasiaca, Tomicus piniperda*, etc.

Orthoptera:

*Locusta migratoria, Gryllotalpa africana, Oxya yezoensis, Oxya japonica*, etc.

Hymenoptera:

*Athalia rosae, Acromyrmex* spp., *Solenopsis* spp., etc.

Blattodea:

*Blattella germanica, Periplaneta fuliginosa, Periplaneta americana, Periplaneta brunnea, Blatta orientalis*, etc.

Acarina:

Tetranychidae such as *Tetranychus urticae, Panonychus citri*, and *Oligonychus* spp.; Eriophyidae such as *Aculops pelekassi*; Tarsonemidae such as *Polyphagotarsonemus latus; Tenuipalpidae; Tuckerellidae*; Acaridae such as *Tyrophagus putrescentiae*; Pyroglyphidae such as *Dermatophagoides farinae*, and *Dermatophagoides ptrenyssnus*; Cheyletidae such as *Cheyletus eruditus, Cheyletus malaccensis*, and *Chelacaropsis moorei*; etc.

Nematoda:

*Aphelenchoides besseyi, Nothotylenchus acris*, etc.

The pest control method of the present invention comprises applying effective amounts of etoxazole and the compound represented by the formula (I) to a pest or an area where a pest lives.

Examples of the area where a pest lives include crops and soil where crops are grown.

The pest control method of the present invention can be carried out by applying the pest control composition of the present invention to a pest or an area where a pest lives. The pest control method of the present invention can be also carried out by applying etoxazole and the compound represented by the formula (I) separately to a pest or an area where a pest lives.

In the pest control method of the present invention, the weight ratio of etoxazole to the compound represented by the formula (I) is within the range from usually 100:1 to 1:100, preferably 10:1 to 1:10, more preferably 5:1 to 1:5.

In the pest control method of the present invention, application of etoxazole and the compound represented by the formula (I) can be carried out by, for example, spraying the foliage of crops with etoxazole and the compound represented by the formula (I), irrigating soil where crops are grown with etoxazole and the compound represented by the formula (I), or treating the seeds of crops with etoxazole and the compound represented by the formula (I).

Herein, the "effective amounts" mean the total amount of etoxazole and the compound represented by the formula (I) in which amount the application of both compounds can make a pest controlled.

When etoxazole and the compound represented by the formula (I) are applied to the foliage of crops or the soil where crops are grown, the application rate is usually from 0.1 to 1000 g per 10000 $m^2$, preferably from 1 to 200 g per 10000 $m^2$, in terms of the total amount of etoxazole and the compound represented by the formula (I), although it may be varied depending on the kinds of crops to be protected from pests, the kinds of target pests, the population size of target pests, the type of a formulation, the application period, and climate conditions.

When etoxazole and the compound represented by the formula (I) are formulated into an emulsifiable concentrate, a wettable powder or a suspension concentrate, the formulation is usually diluted with water and then sprayed. In this case, the formulation is diluted so that the total concentration of etoxazole and the compound represented by the formula (I) becomes usually from 1 to 1000 ppm, preferably from 10 to 500 ppm.

When etoxazole and the compound represented by the formula (I) are formulated into a dust or a granule, the formulation is usually applied as it is without diluting it.

When the seeds of crops are treated with etoxazole and the compound represented by the formula (I), the treatment rate is usually from 0.001 to 20 g, preferably from 0.01 to 10 g per 1 kg of seeds, in terms of the total amount of etoxazole and the compound represented by the formula (I).

The pest control composition of the present invention can be used in pest control for plants including, but not limited to, "crops" listed below.

"Crops":

Agricultural crops: corn, wheat, barley, rye, oat, sorghum, cotton, soybean, rice, peanut, sarrazin, sugar beet, rapeseed, sunflower, sugar cane, tobacco etc.;

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, chard, etc.), Labiatae vegetables (Japanese basil, mint, basil, etc.), strawberry, sweat potato, yam, aroid etc.;

Flowers and ornamental plants: *acanthus*, morning glory, azalea, hydrangea, *anemone raddeana, rhodohypoxis baurii, anemone, polygonatum odoratum*, amaryllis, iris, *alyssum, armeria, arctotis*, China aster, edible flower, *Bauera ruibioides*, Cuban lily, *Hosta montana*, Mexican aster, four o'clock, *Hypericum*, oriental poppy, *gentiana makinoi, Hosta aureomarginata*, Japanese iris, *clematis patens, gazania*, Casa Blanca, carnation, showy lily, *gerbera, kalanchoe, calceolaria*, curry plant, Carolina jasmine, *canna, chrysanthemum, Brugmansia*, yellow cosmos, plantain lily, KimJongilia, tea tree (Manuka), pot marigold, myrtle, *nasturtium, gladiolus*, Siam tulip, *clematis*, cockscomb, shrimp plant, midday flower, *cosmos, Hosta sieboldii, Convolvulus arvensis, Hosta sagae*, primrose, saffron crocus, *salvia, cyclamen*, moss phlox, *Paeonia lactiflora, Anemone hupehensis, Bletilla striata*, sweet pea, lily of the valley, snowflake, *portulaca*, violet, rose of Sharon, yarrow, Chinese pink, *zephyranthes, pelargonium, geum*, zepher lily, *dahlia, tithonia*, tulip, chocolate cosmos, *Vinca major, scilla*, downy myrtle, German iris, passionflower, *dianthus*, rape blossom, Madagascar periwinkle, soft windflower, *nemophila, Nerine*, swamp chrysanthemum (North pole), Japanese water iris (*iris ensata* var. *spontanea*), *verbena, hibiscus*, Joseph's coat, coral flower, Japanese water iris (*Iris ensata*), eastern redbud, spring starflower, wavyleaf sea-lavender, California poppy, pansy, Virginia stock, daisy, corn poppy, Himalayan creeping saxifrage, sunflower, *hyacinth*, crape-myrtle, *Geranium, fuchsia, freesia, primula*, garden balsam, ground-cherry, peony, *Tricyrtis, marguerite*, marigold, *Gymnaster savatieri*, strawflower, *muscari*, Japanese kerria, lily, *ranunculus, lantana*, gentian, *Lupinus, lobelia*, etc.;

Ornamental foliage plants: ivy, cat tail, *aglaonema, adiantum, asparagus, asplenium, ananas, aphelandra, alocasia, anthurium*, Indian rubber tree, *nepenthes, aechmea, aeschynanthus, episcia, strelitzia augusta*, spiders plant, Chinese banyan, kapok, *caladium, calathea*, velvet plant (*Gynura*), *Guzumania, Ctenanthe*, gum tree, *crassula, croton, Alocasia odora*, orange jessamine, coffee tree, *massangeana*, conifers, *coleus, cordyline, columnea, sansevieria, sansevieria*, Chinese ixora, *schefflera, cissus, cyperus, reed rhapis*, silk jessamine, *syngonium, strelitzia, spathiphyllum, senecio, zebrina*, Japanese sago palm, *tillandsia, tupidanthus*, coral tree, *dizygotheca, dieffenbachia, duranta*, bottle palm, *dracaena, tradescantia, neoregelia, nephrolepis*, hearts vine, *hibiscus, pachypodium*, Guiana chestnut (*Pachira*), ponytail, staghorn fern, *pilea, fatshedera, ficus pumila, philodendron, bougainvillea, phoenix, fittonia, pteris*, bridal veil, *vriesea, plectranthus, begonia, peperomia, heliconia, benjamina, poinsettia, pothos, hoya, maranta*, Belgian evergreen, milkbush, oyster plant, *monstera*, palm, *yucca, lantana*, etc.;

Fruit trees: pomaceous fruits (apple, common pear, Japanese pear, Chinese quince, quince, etc.), stone fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nut, almond, pistachio, cashew nut, *macadamia* nut, etc.), berry fruits (blueberry, cranberry, blackberry, raspberry, etc.), grape, persimmon, olive, loquat, banana, coffee, date, coconut, etc.;

Trees other than fruit trees: tea, mulberry, flowering trees and shrubs, street trees (ash tree, birch, dogwood, *eucalyptus, ginkgo*, lilac, maple tree, oak, poplar, *cercis*, Chinese sweet gum, plane tree, *zelkova*, Japanese arborvitae, fir tree, Japanese hemlock, needle juniper, pine, spruce, yew), etc.

The above-described "crops" include plants having the resistance to herbicides which is imparted by a classic breeding method or a genetic engineering technique, and the herbicides include 4-hydroxyphenylpyruvate dioxygenase (hereinafter, referred to as "HPPD") inhibitors (e.g. isoxaflutole), acetolactate synthase (hereinafter, referred to as "ALS") inhibitors (e.g. imazethapyr, and thifensulfuron-methyl), 5-enolpyruvyl-shikimate-3-phosphate synthetase (hereinafter, referred to as "EPSP") inhibitors (e.g. glyphosate), glutamine synthetase inhibitors (e.g. glufosinate), auxin-type herbicides (e.g. 2,4-D, and dicamba), and bromoxynil.

Examples of the "crops" having the resistance imparted by a classic breeding method include corn and canola resistant to imidazolinone-type ALS inhibitors (e.g. imazethapyr), which are already on the market under the trade name of Clearfield (registered trademark); STS soybean resistant to sulfonylurea-type ALS inhibitors (e.g. thifensulfuron-methyl); and SR corn resistant to acetyl CoA carboxylase inhibitors such as trione oxime-type herbicides and aryloxyphenoxypropionic acid-type, herbicides. For example, plants having the resistance to acetyl CoA carboxylase inhibitors are found in Proc. Natl. Acad. Sci. USA 1990, 87, pp. 7175-7179.

Examples of the "crops" having the resistance imparted by a genetic engineering technique include corn, soybean, and cotton resistant to glyphosate and glufosinate, which are already on the market under the trade names of RoundupReady (registered trademark), LibertyLink (registered trademark), and Optimum GAT (registered trademark).

A mutant acetyl CoA carboxylase which provides the resistance to an acetyl CoA carboxylase inhibitor is reported, for example, in Weed Science vol. 53, pp. 728-746 (2005). A plant having the resistance to an acetyl CoA carboxylase inhibitor can be produced by introducing a gene encoding the mutant acetyl CoA carboxylase into a plant by a genetic engineering technique or by introducing a mutation related to impartation of resistance into a gene encoding acetyl CoA carboxylase of a plant. In addition, nucleic acids for introduction of a base substitution mutation can be introduced into a plant cell by chimeraplasty technique (see, Gura T., Repairing the Genome's Spelling Mistakes, Science vol. 285, p. 316-318 (1999)) to induce a site-directed amino acid mutation in a plant gene to be targeted by a herbicide, such as a gene encoding acetyl CoA carboxylase or a gene encoding ALS, and thereby a herbicide-resistant plant can be produced.

A plant having the resistance to dicamba can be produced by introducing a dicamba degrading enzyme such as dicamba monooxygenase isolated from *Pseudomonas maltophilia* into a plant (see, Behrens et al., 2007 Dicamba Resistance: Enlarging and Preserving Biotechnology-Based Weed Management Strategies. Science 316: 1185-1188).

A gene encoding aryloxyalkanoate dioxygenase can be introduced into a plant to produce a plant having the resistance to both phenoxy acid-type herbicides such as 2,4-D, MCPA, dichlorprop, and mecoprop; and aryloxyphenoxypropionic acid-type herbicides such as quizalofop, haloxyfop, fluazifop, diclofop, fenoxaprop, metamifop, and cyhalofop (see, WO2005/107437, WO2007/053482, and WO2008/141154).

The above-described "crops" also include plants having the ability to produce an insecticidal toxin, for example a selective toxin originated from *Bacillus*, which ability is imparted by a genetic engineering technique.

Examples of insecticidal toxins produced in such genetically engineered plants include insecticidal proteins derived from *Bacillus cereus* and *Bacillus popilliae*; insecticidal proteins such as δ-endotoxins derived from *Bacillus thuringiensis* (e.g. Cry1Ab, Cry1Ac, Cry1F, Cry1Fa2, Cry2Ab, Cry3A, Cry3Bb1 and Cry9C), VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, luffin, saporin, and bryodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl synthase; chitinase; and glucanase.

The toxins produced in such genetically engineered plants also include hybrid toxins, partly deficient toxins and modified toxins of insecticidal proteins such as δ-endotoxin proteins (e.g., Cry1Ab, Cry1Ac, Cry1F, Cry1Fa2, Cry2Ab, Cry3A, Cry3Bb1 and Cry9C), VIP1, VIP2, VIP3, and VIP3A. The hybrid toxin is made by combining different domains of the insecticidal proteins by a genetic engineering technique.

An example of the partly deficient toxin includes Cry1Ab in which a part of amino acids is deleted. An example of the modified toxin includes a toxin in which one or more of amino acids of a naturally occurring toxin are substituted.

Examples of the insecticidal toxin and the genetically engineered crop plant having the ability to produce the insecticidal toxin are described, for example, in EP-A-0 374 753, WO 93/07278, WO 95/34656, EP-A-0 427 529, EP-A-451878, or WO 03/052073.

The genetically engineered plant having the ability to produce the insecticidal toxin particularly has the resistance to attack by coleopteran pests, dipteran pests and lepidopteran pests.

Genetically engineered plants which have one or more insecticidal pest-resistance genes and thereby produce one or more toxins are also known, and some of them are commercially available. Examples of such genetically engineered plants include YieldGard (registered trademark) (a corn cultivar expressing Cry1Ab toxin), YieldGard Rootworm (registered trademark) (a corn cultivar expressing Cry3Bb1 toxin), YieldGard Plus (registered trademark) (a corn cultivar expressing Cry1Ab and Cry3Bb1 toxins), Herculex I (registered trademark) (a corn cultivar expressing Cry1Fa2 toxin and phosphinothricin N-acetyltransferase (PAT) for imparting resistance to glufosinate), NuCOTN33B (registered trademark) (a cotton cultivar expressing Cry1Ac toxin), Bollgard I (registered trademark) (a cotton cultivar expressing Cry1Ac toxin), Bollgard II (registered trademark) (a cotton cultivar expressing Cry1Ac and Cry2Ab toxins), VIPCOT (registered trademark) (a cotton cultivar expressing VIP toxin), NewLeaf (registered trademark) (a potato cultivar expressing Cry3A toxin), NatureGard Agrisure GT Advantage (registered trademark) (GA21 glyphosate-resistance character), Agrisure CB Advantage (registered trademark) (Bt11 corn borer (CB) character), and Protecta (registered trademark).

Examples of plants to be protected from pests by the pest control composition or the pest control method of the present invention include plants in which a Rag1 gene (Resistance Aphid Gene 1) is introduced and whereby the resistance to aphids is imparted.

The above-described "crops" also include plants having the ability to produce anti-pathogen substances which is imparted by a genetic engineering technique.

Examples of the anti-pathogen substance include PR proteins (PRPs, described in EP-A-0 392 225); ion channel inhibitors such as sodium channel inhibitors, and calcium channel inhibitors (e.g. KP1, KP4, and KP6 toxins produced by viruses); stilbene synthase; bibenzyl synthase; chitinase; glucanase; and anti-pathogen substances produced by microorganisms such as peptide antibiotics, heterocycle-containing antibiotics, and protein factors involved in plant disease-resistance (referred to as plant disease-resistance genes, and described in WO03/000906). Such anti-pathogen substances and genetically engineered plants which produce the anti-pathogen substances are described in EP-A-0 392 225, WO 95/33818, or EP-A-0 353 191.

The above-described "crops" include plants having beneficial traits such as a modified oil component and an enhanced amino acid content which are imparted by a genetic engineering technique. Examples of such plants include VISTIVE (registered trademark) (low linolenic soybean which has a reduced content of linolenic acid), and high-lysine (high-oil) corn (corn which has an increased content of lysine or oil).

Furthermore, the above-described "crops" include stacked plant varieties which have a combination of two or more of beneficial traits such as the above-described classical herbicide-resistant trait and herbicide-resistance gene, an insecticidal pest-resistant gene, an anti-pathogen substance-producing gene, a modified oil component, and an enhanced amino acid content.

The present invention also relates to use of a combination of etoxazole and the compound represented by the formula (I) for the production of a pest control agent.

The present invention also relates to use of a combination of etoxazole and the compound represented by the formula (I) in pest control.

In the present invention, etoxazole and the compound represented by the formula (I) may be used in admixture with or in combination with other active ingredients such as other insecticides, acaricides, nematocides, fungicides, herbicides, plant hormones, and plant growth regulators; synergists; safeners; pigments, fertilizers; soil conditioners; and/or animal feed.

EXAMPLES

Hereinafter, the present invention is described specifically by way of Formulation Examples and Test Examples to which the present invention is not limited.

First, Formulation Examples are described. In Examples, the term "part(s)" means part(s) by weight.

Formulation Example 1

Five parts of etoxazole, 5 parts of spinosad or spinetoram, 8 parts of polyoxyethlene styrylphenyl ether, 2 parts of calcium dodecylbenzenesulfonate, and 80 parts of xylene are mixed to obtain an emulsifiable concentrate.

Formulation Example 2

A mixture of 20 parts of etoxazole, 4 parts of spinosad or spinetoram, 3 parts of sodium dodecylbenzenesulfonate, 3 parts of sodium ligninsulfonate, and 70 parts of diatomaceous earth is pulverized in a jet air mill to obtain a wettable powder.

Formulation Example 3

One part of etoxazole, 0.5 part of spinosad or spinetoram, 48.5 parts of talc, and 50 parts of clay are mixed to obtain a dust.

Formulation Example 4

A mixture of 1 part of etoxazole, 4 parts of spinosad or spinetoram, 5 parts of sodium dodecylbenzenesulfonate, 30 parts of bentonite, and 60 parts of clay is stirred with an appropriate amount of water, granulated in a granulator, and then dried under ventilation to obtain a granule.

Formulation Example 5

To a mixture of 5 parts of polyoxyethylene styrylphenyl ether sulfate, 20 parts of a 1% aqueous xanthan gum solution, 3 parts of a smectite mineral, and 60 parts of water are added 5 parts of etoxazole and 5 parts of spinosad or spinetoram. The mixture is stirred and then wet ground in a sand mill to obtain a suspension concentrate.

Formulation Example 6

A solution of 0.1 part of etoxazole and 0.02 parts of spinosad or spinetoram in 10 parts of acetone is uniformly mixed with 99.88 parts of animal solid feed powder (CE-2: a solid powdery diet for growing and breeding manufactured by CLEA Japan, Inc.), and then the acetone is removed by air drying to obtain a poison bait.

Formulation Example 7

A solution of 0.1 part of etoxazole and 0.1 part of spinosad or spinetoram in 5 parts of xylene and 5 parts of trichloroethane is mixed with 89.9 parts of deodorized kerosene to obtain an oil solution.

Next, Test Examples for pest control by the present invention are described.

Test Example 1

A suspension concentrate containing 10.0% by weight of etoxazole [product name: Baroque (registered trademark) flowable, manufactured by Kyoyu Agri Co., Ltd.] was diluted with water containing 0.02% by volume of a spreading agent [product name: Sindain (registered trademark), manufactured by Sumitomo Chemical Co., Ltd.] so that the concentration of etoxazole became 25 ppm.

A suspension concentrate containing 11.7% by weight of spinetoram (weight ratio of spinetoram J:spinetoram L=75:25) was diluted with water containing 0.02% by volume of a spreading agent [product name: Sindain (registered trademark), manufactured by Sumitomo Chemical Co., Ltd.] so that the concentration of spinetoram became 7.31 ppm.

The water dilution of spinetoram was mixed with an equal amount of the water dilution of etoxazole to prepare a test solution.

The water dilution of etoxazole and the water dilution of spinetoram were respectively diluted with an equal amount of water containing 0.02% by volume of the same spreading agent as mentioned above to prepare a 12.5 ppm water dilution of etoxazole and a 3.66 ppm water dilution of spinetoram.

A cabbage was planted in a pot (volume: 860 ml) and grown until the fourth leaf stage. The leaves of the cabbage were cut off one by one. One of the leaves was immersed in the test solution for 60 seconds. After air drying, the cabbage leaf was placed in a cup (volume: 500 ml) with a filter paper spread on the bottom. Similarly, one of the cabbage leaves was treated with the 12.5 ppm water dilution of etoxazole or the 3.66 ppm water dilution of spinetoram, air dried, and then placed in a cup. Into each cup, 10 third-instar larvae of *Spodoptera litura* were released. These are called treated-sections.

On the other hand, the same experiment as mentioned above was performed except that a cabbage leaf was not immersed in any chemical solution. This is called an untreated-section.

After 4 days, the tested larvae were observed for life or death in the treated-sections and the untreated-section. An insect death rate was calculated according to the following equation.

Insect death rate(%)=100×(number of tested insects−number of surviving insects)/number of tested insects Insect death rates were corrected according to the following equation to obtain an insecticidal rate.

Insecticidal rate(%)=100×($Mt-Mc$)/(100−$Mc$)

Mt: Insect death rate (%) in a treated-section
Mc: Insect death rate (%) in an untreated-section For each treatment there were 3 replicates. Results are shown in Table 2.

TABLE 2

| Active ingredient | Concentration of Active ingredient (ppm) | Insecticidal rate (%) |
| --- | --- | --- |
| Etoxazole + Spinetoram | 12.5 + 3.66 | 93.3 |
| Etoxazole | 12.5 | 26.7 |
| Spinetoram | 3.66 | 43.3 |

Test Example 2

A suspension concentrate containing 10.0% by weight of etoxazole [product name: Baroque (registered trademark) flowable, manufactured by Kyoyu Agri Co., Ltd.] was diluted with water containing 0.02% by volume of a spreading agent [product name: Sindain (registered trademark), manufactured by Sumitomo Chemical Co., Ltd.] so that the concentration of etoxazole became 1.56 ppm.

A suspension concentrate containing 11.7% by weight of spinetoram (weight ratio of spinetoram J:spinetoram L=75:25) was diluted with water containing 0.02% by volume of a spreading agent [product name: Sindain (registered trademark), manufactured by Sumitomo Chemical Co., Ltd.] so that the concentration of spinetoram became 6.25 ppm.

The water dilution of spinetoram was mixed with an equal amount of the water dilution of etoxazole to prepare a test solution.

The water dilution of etoxazole and the water dilution of spinetoram were respectively diluted with an equal amount of water containing 0.02% by volume of the same spreading agent as mentioned above to prepare a 0.78 ppm water dilution of etoxazole and a 3.13 ppm water dilution of spinetoram.

Leaves were taken from a cultivated Satsuma mandarin orange tree, and cut into 2-cm-square pieces. One of the pieces was immersed in the test solution for 60 seconds. After air drying, the piece was placed on absorbent cotton saturated with water. Similarly, one of the pieces was treated with the 0.78 ppm water dilution of etoxazole or the 3.13 ppm water dilution of spinetoram, air dried, and then placed on absorbent cotton saturated with water. On each piece, 10 female imagoes of *Panonychus citri* were released. These are called treated-sections.

On the other hand, the same experiment as mentioned above was performed except that a piece of a Satsuma mandarin orange leaf was not immersed in any chemical solution. This is called an untreated-section.

After 6 days, the tested imagoes were observed for life or death in the treated-sections and the untreated-section. An insecticidal rate was calculated in the same manner as Test Example 1.

For each treatment there were 3 replicates. Results are shown in Table 3.

TABLE 3

| Active ingredient | Concentration of Active ingredient (ppm) | Insecticidal rate (%) |
| --- | --- | --- |
| Etoxazole + Spinetoram | 0.78 + 3.13 | 92.3 |
| Etoxazole | 0.78 | 7.7 |
| Spinetoram | 3.13 | 23.1 |

Test Example 3

A suspension concentrate containing 10.0% by weight of etoxazole [product name: Baroque (registered trademark)

flowable, manufactured by Kyoyu Agri Co., Ltd.] is diluted with water containing 0.02% by volume of a spreading agent [product name: Sindain (registered trademark), manufactured by Sumitomo Chemical Co., Ltd.] so that the concentration of etoxazole becomes 100 ppm.

A suspension concentrate containing 11.7% by weight of spinetoram (weight ratio of spinetoram J:spinetoram L=75:25) is diluted with water containing 0.02% by volume of a spreading agent [product name: Sindain (registered trademark), manufactured by Sumitomo Chemical Co., Ltd.] so that the concentration of spinetoram becomes 93.6 ppm.

The water dilution of spinetoram is mixed with an equal amount of the water dilution of etoxazole to prepare a test solution.

A cabbage is planted in a pot (volume: 860 ml) and grown until the fourth leaf stage. The leaves of the cabbage are cut off one by one. One of the leaves is immersed in the test solution for 60 seconds. After air drying, the cabbage leaf is placed in a cup (volume: 500 ml) with a filter paper spread on the bottom. Into each cup, 10 third-instar larvae of *Spodoptera litura* are released. This is called a treated-section.

On the other hand, one of the cabbage leafs without immersing in the test solution and air drying is placed in a cup (volume: 500 ml) with a filter paper spread on the bottom. Into each cup, 10 third-instar larvae of *Spodoptera litura* are released. This is called an untreated-section.

After 4 days, the tested larvae are observed for life or death in the treated-section and the untreated-section. An insect death rate is calculated according to the following equation.

Insect death rate(%)=100×(number of dead insects/number of tested insects)

An insect death rate is corrected according to the following equation to obtain an insecticidal rate. For each treatment there are 3 replicates.

Insecticidal rate(%)=100×(*Mt*−*Mc*)/(100−*Mc*)

Mt: Insect death rate (%) in a treated-section
Mc: Insect death rate (%) in an untreated-section As a result of the test, it is found that the test solution shows a high insecticidal rate.

The invention claimed is:

1. A pest control composition comprising etoxazole and a compound represented by the formula (I):

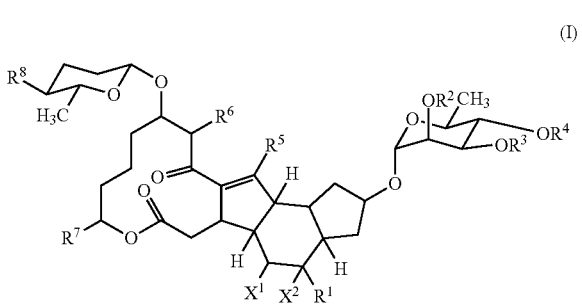

(I)

wherein,
R$^1$ is a hydrogen atom or a methyl group,
R$^2$ is a hydrogen atom, a C1-C4 alkyl group, a C1-C4 haloalkyl group, or a (C1-C4 alkyl)carbonyl group,
R$^3$ is a hydrogen atom, a C1-C4 alkyl group, a C1-C4 haloalkyl group, or a (C1-C4 alkyl)carbonyl group,
R$^4$ is a hydrogen atom, a C1-C4 alkyl group, a C1-C4 haloalkyl group, or a (C1-C4 alkyl)carbonyl group,
R$^5$ is a hydrogen atom, a C1-C4 alkyl group, or a C1-C4 alkylamino group,
R$^6$ is a hydrogen atom or a methyl group,
R$^7$ is a methyl group or an ethyl group,
R$^8$ is an amino group, a C1-C4 alkylamino group, or a di(C1-C4 alkyl)amino group, and
X$^1$ and X$^2$ are hydrogen atoms or X$^1$ and X$^2$ together form a single bond.

2. The pest control composition according to claim 1, wherein the weight ratio of etoxazole to the compound represented by the formula (I) is 100:1 to 1:100.

3. The pest control composition according to claim 1 or 2, wherein the compound represented by the formula (I) is spinosad or spinetoram.

4. A pest control method which comprises applying effective amounts of etoxazole and a compound represented by the formula (I) to a pest or an area where a pest lives:

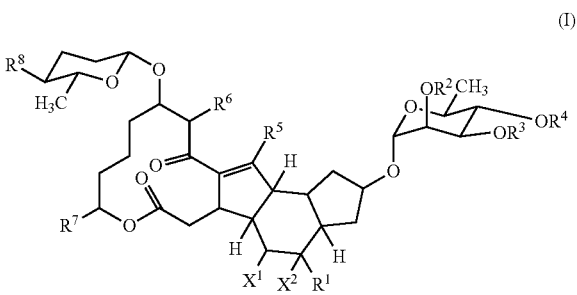

(I)

wherein,
R$^1$ is a hydrogen atom or a methyl group,
R$^2$ is a hydrogen atom, a C1-C4 alkyl group, a C1-C4 haloalkyl group, or a (C1-C4 alkyl)carbonyl group,
R$^3$ is a hydrogen atom, a C1-C4 alkyl group, a C1-C4 haloalkyl group, or a (C1-C4 alkyl)carbonyl group,
R$^4$ is a hydrogen atom, a C1-C4 alkyl group, a C1-C4 haloalkyl group, or a (C1-C4 alkyl)carbonyl group,
R$^5$ is a hydrogen atom, a C1-C4 alkyl group, or a C1-C4 alkylamino group,
R$^6$ is a hydrogen atom or a methyl group,
R$^7$ is a methyl group or an ethyl group,
R$^8$ is an amino group, a C1-C4 alkylamino group, or a di(C1-C4 alkyl)amino group, and
X$^1$ and X$^2$ are hydrogen atoms or X$^1$ and X$^2$ together form a single bond.

5. The pest control method according to claim 4, wherein the weight ratio of etoxazole to the compound represented by the formula (I) is 100:1 to 1:100.

6. The pest control method according to claim 4 or 5, wherein the compound represented by the formula (I) is spinosad or spinetoram.

* * * * *